United States Patent [19]

Yano et al.

[11] Patent Number: 4,657,896

[45] Date of Patent: Apr. 14, 1987

[54] METHOD FOR THE TREATMENT OF DIGESTIVE ULCERS

[75] Inventors: Osamu Yano; Takafumi Kitano, both of Chiba, Japan

[73] Assignee: Mitsui Toatsu Chemicals, Inc., Tokyo, Japan

[21] Appl. No.: 611,160

[22] Filed: May 17, 1984

[30] Foreign Application Priority Data

May 30, 1983 [JP] Japan .................................. 58-94141

[51] Int. Cl.$^4$ ............................................ A61K 31/73
[52] U.S. Cl. ..................................................... 514/44
[58] Field of Search .................. 424/180, 181; 536/27, 536/28, 29; 514/44

[56] References Cited

U.S. PATENT DOCUMENTS

| | | | |
|---|---|---|---|
| 3,534,017 | 10/1970 | Fujimoto et al. | 536/27 |
| 4,054,648 | 10/1977 | Nagasawa et al. | 424/105 |
| 4,190,649 | 2/1980 | Beljanski | 424/180 |
| 4,579,941 | 4/1986 | Furutani et al. | 536/27 |

OTHER PUBLICATIONS

Konturek et al, Role of Mucosal Prostaglandins and DNA Synthesis in Gastric Cytoprotection ..., Chem. Abstracts 96: 174783e, (1981).

Loeb et al, Suppression of Thymidine Incorporation into the Gastric Mucose of Cortisone-Treated Rats ..., Chem. Abstracts 79: 38782a, (1973).

Manicheva et al, Effect of Plant Drugs on the Nucleic Acid Content of Gastric Tissues During Ulcerogenosis, Chem. Abstracts 101: 17125w, (1984).

Akita, Experimental Studies of the Effect of Anti-Ulcer Drugs on the Gastric Ulcer in Rats, Chem. Abstracts 88: 32078g, (1977).

Virabyan et al, Comparative Antiulcer Efficacy of Sodium Nucleate, Tocopherol and Quateron, Chem. Abstracts 101: 143895k, (1984).

Bradley, Reassociation of DNA from Selected Mycobacteria with that from Mycobacterium bovis and Mycobacterium Faranica, Chem. Abstracts 77: 123088g, (1972).

Sikorska et al., Isolation and Some Properties of Deoxyribonucleic Acids from Mycobacterium Tuberculosis BCG, Chem. Abstracts 71: 45873u, (1969).

Klebanova et al., Immunogenic Characteristics of Deoxyribonucleic Acid of BCG Cultures, Chem. Abstracts 82: 153656m, (1973).

Pitha, Nucleic Acids and Sulfate and Phosphate Polyanions, Chem. Abstracts 95: 89x, (1980).

Svistun et al., Role of the Nucleic Acids and Proteins for the Gastric Mucosa in the Secretory Process, Chem. Abstracts 94: 136612z, (1981).

Chemical Abstracts 98: 65456w, (1983).

*Primary Examiner*—Johnnie R. Brown
*Attorney, Agent, or Firm*—Browdy and Neimark

[57] ABSTRACT

DNAs, the salts thereof, the mixtures of DNA and RNA in which the DNA is mostly contained, and the mixtures of the salt of DNA and the salt of RNA in which the salt of DNA is mostly contained are used as active ingredients for pharmaceutical preparations for digestive ulcer, for example, DNA and RNA being obtained from BCG.

9 Claims, No Drawings

METHOD FOR THE TREATMENT OF DIGESTIVE ULCERS

DETAILED DESCRIPTION OF THE INVENTION

The present invention relates to a pharmaceutical preparation for the treatment of digestive ulcers, containing as active ingredient deoxyribonucleic acid or salts thereof.

The number of patients with digestive ulcer are increasing these days as a result of enhanced mental stress caused by complication of social life. Much of the mechanism and pathophysiology of digestive ulcer is yet unknown, and no decisive therapeutic method for this disease has yet been established.

Digestive ulcer is at present treated principally by pharmacotherapeutic means, wherein antacids, antipeptic agents, or anticholinergic agents are used against digestive tract-attacking factors represented by gastric acid and pepsin.

On the other hand, it is assumed that in a living organism, the onset of digestive ulcer may be accompanied by the exercise of an anti-ulcer therapeutic mechanism, which is considered as one of the protective abilities endowed with living organisms. The idea of this protective ability of living organisms is now attracting interest, and some approaches have been made to encourage this ability, thereby accelerating the therapy of ulcer. Extracts from vegetable or animal tissues and synthetic compounds have been found in line with this approach. In recent years, expectations have been enhanced particularly for the medicaments in this field.

As pharmaceutical preparations are usually employed in combination in the therapy of digestive ulcer, the development of medicament is desired that have different characteristics in action and physical properties from those conventionally employed.

Moreover, there is a problem of side-effects when medicaments are administered for a prolonged period to prevent the recurrence of digestive ulcer, which has a high recurrence ratio.

Much of the pharmacological effects of nucleic acid, which is used in the present invention is unknown, and almost nothing has been tried regarding its medical application. The present inventors have been interested in the medical application of nucleic acid, and as a result of intensive studies have filed in a patent application (see Japanese Patent Laid-Open No. 139096/1982) disclosing the remarkable host-mediated antitumor effect, as well as excellent safety, of nucleic acid, particularly deoxyribonucleic acid.

In the process of the present study, the inventors examined the intracorporeal distribution of nucleic acid administered to a living organism. It was notedly observed that nucleic acid was distributed in relatively high concentration in the digestive tracts centering around the stomach. As a result of intensive studies regarding the pharmacological effects of nucleic acid on digestive tracts, the inventors have completed the present invention based on the finding that nucleic acid remarkably accelerates the cure of digestive ulcer. It has never been reported heretofore that nucleic acid shows the above-mentioned effect.

Accordingly, the present invention relates to a pharmaceutical preparation for digestive ulcer containing, as active ingredient, nucleic acid or salts thereof, and more particularly, to a pharmaceutical preparation for digestive ulcer containing as active ingredient nucleic acid or salts thereof obtained from BCG.

The present invention further relates to a pharmaceutical preparation for digestive ulcer containing as active ingredient deoxyribonucleic acid or salts thereof, and more particularly to a pharmaceutical preparation for digestive ulcer containing as active ingredient deoxyribonucleic acid or salts thereof obtained from BCG.

The present invention further relates to a pharmaceutical preparation for digestive ulcer containing as active ingredient a mixture of deoxyribonucleic acid and ribonucleic acid principally comprising deoxyribonucleic acid or salts thereof, and more particularly to a pharmaceutical preparation for digestive ulcer containing as active ingredient a mixture of deoxyribonucleic acid and ribonucleic acid principally comprising deoxyribonucleic acid or salts thereof obtained from BCG.

The nucleic acid to be used in the present invention includes that prepared from known calf thymus, salmon testes, microorganisms, or other natural products, among which those which have been already applied to food or medicaments are preferred from the viewpoint of safety. So-called artificially prepared nucleic acids, which are obtained by chemical or biochemical methods, can also be employed. They are represented by deoxyribonucleic acid, ribonucleic acid, mixtures of them, or fractions containing them. It is advisable that the pharmacological and physicochemical properties of each nucleic acid are consistent with the object of the present invention and the amount of impurities that may bring about fever or other side effects contained in said nucleic acid is as small as possible. These nucleic acids may further be subjected to heating, alkaline treatment, or other physicochemical treatments, or nuclease treatment or other biochemical treatments to be more suited as material for pharmaceutical preparation. Heat treatment is particularly preferable because of the ease of operation. The object of these treatments is to improve the effect of nucleic acid as the active ingredient of the pharmaceutical preparation of the present invention, to facilitate the preparation, and further to heighten the solubility of said nucleic acid when it is administered. These treatments, however, are not critical to accomplish the objects of the present invention.

Methods of the preparation of nucleic acid will now be described as Referential Examples.

REFERENTIAL EXAMPLE 1

Preparation of BCG-derived nucleic acid

*Mycobacterium bovis* BCG, ATCC 19015, was statically cultured on a meat extract glycerin medium at 37° C. for 3 weeks, and the culture medium was centrifuged to obtain wet bacilli. 3.3 kg of said wet bacilli was suspended in a 7-fold amount of a 10 mM phosphate buffer solution (pH 7.0) and disrupted under ice-cooling with a DYNO-MILL (trade name) followed by centrifuge at 20,000×g for 20 minutes to obtain 21 l of cell extract. 63 g of streptomycin sulfate was added to said extract, mixed with sufficient agitation and left to stand overnight at 4° C., and the formed precipitates were separated by centrifuge and suspended in a 10 mM phosphate buffer (pH 7.0) containing 0.5 M NaCl. This suspension was dialyzed against the same buffer and then against distilled water to obtain 8 l of a suspension containing nucleic acid.

An equal amount of a 1.8% NaCl was added to 1 l of the suspension, mixed under stirring, and heated at 100°

C. for 60 minutes. After the suspension was cooled, it was centrifuged at 10,000×g for 20 minutes and the supernatant was separated, whereto NaCl was added so that the final concentration was 0.4 M, and agitated. Cetyltrimethylammonium bromide (manufactured by Tokyo Kasei Kogyo) was further added to the solution so that the final concentration was 0.2% (w/v), mixed with sufficient agitation, and left to stand at room temperature for 30 minutes. The formed precipitates were collected by centrifuge and dissolved in 400 ml of a 1 M NaCl.

An equal amount of a chloroform-isoamyl alcohol (24:1) mixture was added to said solution, shaken, and centrifuged to separate the aqueous phase. After this operation was further repeated twice, a three-fold amount of 99.5% ethanol was added to the obtained aqueous phase, mixed under stirring, and left to stand overnight at 4° C. The formed precipitates were collected by centrifuge, dissolved in distilled water, dialyzed against distilled water, and freeze-dried to obtain 1.04 g of BCG-derived nucleic acid. The thus obtained nucleic acid comprised 70% of deoxyribonucleic acid, 28% of ribonucleic acid, and trace amounts of other components. After deoxyribonucleic acid and ribonucleic acid had been fractionated (see Schneider, W. C. (1946) J. Biol. Chem. 164, 747), the nucleic acids were subjected to quantitative determination. Deoxyribonucleic acid was determined by the diphenylamine method (see Burton, K. (1956) Biochem. J. 62, 3, 5) with calf thymus deoxyribonucleic acid as a standard, and ribonucleic acid was determined by the orcinol method (see Mejbaum, W. (1939) Hoppe-Seyler's Z. Physiol. Chem. 258, 117) with yeast ribonucleic acid as a standard. (The determinations were performed in the same manner in the following examples.)

REFERENTIAL EXAMPLE 2

Preparation of Bacillus-derived nucleic acid

*Bacillus subtilis*, ATCC 6633, was cultured under shaking on a peptone medium at 37° C. for 6 hours and the culture medium was centrifuged to obtain wet bacilli. 98 g of the wet bacilli obtained was suspended in 100 ml of a phosphate buffer (pH 7.0) and a Bacillus-derived nucleic acid solution was prepared in the same manner as in Referential Example 1. The solution obtained was neutralized with 1N NaOH and freeze-dried to obtain 158 mg of dried sample. 90 mg of it was dissolved in 10 ml of a 0.05 M acetate buffer (pH 4.5), whereto 200 U of ribonuclease T2 (manufactured by Sankyo) dissolved in 2 ml of said buffer was added and incubated at 37° C. for 22 hours.

An equal amount of chloroform-isoamyl alcohol (24:1) mixture was added to the reaction liquid, shaken, and centrifuged to separate the aqueous layer. After this operation was repeated, the total amount of the aqueous layer was loaded on a column (2.5×90 cm) of Sephadex G-100 (manufactured by Pharmacia Fine Chemicals, Inc.) previously equilibrated with a 0.5 M ammonium bicarbonate and eluted with said solution. The fraction containing deoxyribonucleic acid, which had been eluted first, was obtained and dialyzed against distilled water. The dialyzate was neutralized with 1 N NaOH and freeze-dried to obtain 72 mg of a sodium salt of Bacillus-derived nucleic acid.

The nucleic acid thus obtained substantially comprised deoxyribonucleic acid.

REFERENTIAL EXAMPLE 3

The BCG-derived nucleic acid obtained in Referential Example 1 was digested with ribonuclease (manufactured by Sigma Corp.) and further with pronase, and shaken with chloroform for deproteinization. The aqueous phase of this deproteinized nucleic acid was fraction-purified with a column of Sepharose CL 6B (manufactured by Pharmacia Fine Chemicals, Inc.) to be used in the Tests. The deoxyribonucleic acid content of the obtained nucleic acid was not less than 98%.

REFERENTIAL EXAMPLE 4

The BCG-derived nucleic acid obtained in Referential Example 1 was digested with deoxyribonuclease 1 (manufactured by Worthington Corp.) and shaken with chloroform for deproteinization. The aqueous phase of the deproteinized nucleic acid was used in the Tests after being subjected to fraction-purification with Sephadex G-50 (manufactured by Pharmacia Corp.) column. The ribonucleic acid content of the obtained nucleic acid was not less than 98%.

As understood from the results of the Tests shown below, the acceleration of the cure of ulcer is considered to be one of the pharmacological effects of nucleic acid. Moreover, as demonstrated in Tests 1 and 3, the effect of accelerating the cure of ulcer of nucleic acid is mostly attributable to the effect of deoxyribonucleic acid, because less remarkable effects are shown when only ribonucleic acid is administered than when only deoxyribonucleic acid is administered. It is noted, however, that the incorporation of an appropriate amount of ribonucleic acid with deoxyribonucleic acid exerts a slightly greater effect than the use of either one of them above.

The pharmaceutical preparation of the present invention shows a remarkable effect in curing the acetic acid ulcer of rats, which is considered as a morphologically similar model of human ulcer. Moreover, it is understood that the effective dose of the preparation ranges widely.

The pharmaceutical preparations for digestive ulcer of the present invention have extremely low acute toxicity and are safe in antigenicity. It has been confirmed as the result of the Tests that pyrogenicity, pain, prophlogistic properties, or other troubles are so slight as to be neglected in ordinary application as medicament.

The pharmaceutical preparation for digestive ulcer of the present invention can be applied by itself or in combination with ordinarily employed pharmaceutically acceptable additives or excipients. Dose, method, and route of administration are selected according to the case. Generally, it is advisable to administer 0.001 to 100 mg of it in one dose, at one- to seven-day intervals. The route of administration can be selected from intradermal, hypodermic, intramuscular, intravenous, oral, or direct administration to the seat of the disease.

The present invention will be more readily understood by the following Examples and the versatility of the present invention is further demonstrated by the results of the Tests shown below.

EXAMPLE 1

Liquid preparations 100 mg of the BCG-derived nucleic acid obtained in Referential Example 1 was dissolved in 100 ml of phosphate buffered saline (manufactured by Nissui Seiyaku Co.) and filtered under sterile conditions using a Nuclepore filter (0.2 μm; manufactured by Nuclepore Corp.). 1.5 ml portions of the obtained filtrate were poured into vial bottles under sterile conditions to prepare the liquid preparation of the present invention.

EXAMPLE 2

Lyophilized preparations 100 mg of the BCG-derived nucleic acid was dissolved in 100 ml of distilled water for injection, whereto 5 g of mannitol was added and dissolved, and filtered under sterile conditions using a Nuclepore filter (0.2 μm). After 1 ml portions of the obtained filtrate were poured into vial bottles under sterile conditions, the solution was freeze-dried to obtain a lyophilized preparation of the present invention.

Test 1

Effect of nucleic acid on acetic acid ulcer:

Acetic acid ulcer, which is the rat chronic ulcer model, was prepared in the stomachs of male Wistar rats according to the method of Okabe et al. (Okabe, S. et al. Amer. J. Dig. Dis. Vol. 16, 277 (1971)) to examine the effect of a variety of nucleic acids. The nucleic acids dissolved in a physiological saline were hypodermically administered to the backs of the rats 6 times every other day since the day following the operation. The stomachs were delivered on the day following the final administration (the 12th day after the operation) and lightly fixed with formalin, and the major and minor diameters of the ulcerated are were measured. The ulcer index and curative ratio were calculated from the following formulae:

Ulcer index ($mm^2$) = major diameter (mm) × minor diameter (mm)

Curative ratio (%) =

$$\frac{\text{ulcer index of the control animals} - \text{ulcer index of the animals administered with the drug}}{\text{ulcer index of the control animals}} \times 100$$

The results are summarized in Table 1.

TABLE 1

| Sample | Amount of administration in one dose (μg) | Number of animals | Ulcer index (average ± SE: $mm^2$) | Curative ratio (%) |
|---|---|---|---|---|
| Control[a] | — | 8 | 19.4 ± 3.3 | — |
| E. coli-derived DNA[b] | 200 | 7 | 14.0 ± 3.5 | 28 |
| Bacillus-derived NA[c] | 200 | 7 | 12.9 ± 2.6 | 33 |
| Salmon testes-derived DNA[d] | 200 | 7 | 15.8 ± 3.9 | 19 |
| Calf thymus-derived DNA[e] | 200 | 7 | 17.1 ± 3.1 | 12 |
| Bakers yeast-derived RNA[f] | 200 | 7 | 16.5 ± 3.8 | 15 |

[a]Administered with a physiological saline solution alone
[b]The nucleic acid prepared from E. Coli K-12 according to the method of Marmur (see J. Marmur, J. Mol. Biol. Vol. 3, 208 (1961)) was employed
[c]The Baccillus-derived nucleic acid obtained in Referential Example 2 was employed
[d]Salmon testes DNA (Type III, manufactured by Sigma Corp.) was employed
[e]Calf thymus DNA (Type I, manufactured by Sigma Corp.) was employed
[f]Bakers yeast RNA (Type III, manufactured by Sigma Corp.) was employed

Test 2A

Effect of BCG-derived nucleic acid on acetic acid ulcer (Part 1)

The effect of the BCG-derived nucleic acid obtained in Referential Example 1 was examined in the same manner as in Test 1. The results are summarized in Table 2.

TABLE 2

| Amount of administration in one dose (μg) | Number of animals | Ulcer index (average ± SE: $mm^2$) | Curative ratio (%) |
|---|---|---|---|
| 0 | 11 | 15.7 ± 1.7 | — |
| 20 | 11 | 9.3 ± 1.6* | 41 |
| 200 | 10 | 9.0 ± 1.9* | 43 |
| 2,000 | 12 | 9.4 ± 2.4** | 40 |

*$p < 0.02$,
**$p < 0.05$

Test 2B

Effect of BCG-derived nucleic acid on acetic acid ulcer (Part 2)

The effect of the BCG-derived nucleic acid obtained in Referential Example 1 and the deoxyribonucleic acid and ribonucleic acid separated from said BCG-derived nucleic acid were tested in the same manner as in Test 1. The results are summarized in Table 3.

TABLE 3

| Sample | Amount of administration in one dose (μg) | Number of animals | Ulcer index (average ± SE: $mm^2$) | Curative ratio (%) |
|---|---|---|---|---|
| Control[a] | — | 12 | 15.4 ± 1.8 | — |
| BCG-derived NA | 100 | 12 | 8.9 ± 1.3** | 42 |
| BCG-derived DNA[b] | 100 | 12 | 10.6 ± 1.4** | 31 |
| BCG-derived RNA[c] | 100 | 12 | 13.2 ± 2.5 | 14 |

**$P < 0.05$
[a]administered with 5% mannitol
[b]obtained in Referential Example 3
[c]obtained in Referential Example 4

Test 3A

Acute toxicity test of BCG-derived nucleic acid:

The BCG-derived nucleic acid obtained in Referential Example 1 dissolved in a physiological saline solution was intravenously administered at a dose level of 1 g per kg of the body weight to male ddY mice which were 5 weeks of age and divided into groups of 10 animals each (weighing 23 g on the average). During the observation period of one week after the administration, no hindrance of weight increase nor death were observed. It is understood from the result that the 50% lethal dose ($LD_{50}$) of the present substance in intravenous administration is not lower than 1 g/kg.

Test 3B

Acute toxicity test of BCG-derived deoxyribonucleic acid

The acute toxicity of the BCG-derived deoxyribonucleic acid employed in Test 2B was examined in the same manner as in Test 3A. It is understood from the result of the test that the 50% lethal dose ($LD_{50}$) of the present substance in intravenous administration is not lower than 1 kg/kg.

Test 4A

Antigenicity test of BCG-derived nucleic acid

The BCG-derived nucleic acid obtained in Referential Example 1 dissolved in a physiological saline solution was intradermally administered at a dose level of 1 mg per animal to female Hartley guinea pigs which had been divided into groups of 6 animals each (weighing 350 g on the average) 6 times (3 times a week) for sensitization. Two weeks after the final sensitization, the same BCG-derived nucleic acid dissolved in a physiological saline solution was intravenously administered at a dose level of 10 mg or 2 mg per kg of the body weight. It was understood from the result of the examination of the antigenicity of the present substance by observing the guinea pigs' behavior around challenge that no anaphylaxis shock was induced at all at the above dose level.

Test 4B

Antigenicity test of BCG-derived deoxyribonucleic acid

The antigenicity of the BCG-derived deoxyribonucleic acid employed in Test 2B was tested in the same manner as in Test 4A. As the result of the test, it was found that the present substance induced no anaphylactic shock.

What is claimed is:

1. A method for the treatment of digestive ulcers comprising administering to a patient having a digestive ulcer an amount effective to ameliorate the symptoms of digestive ulcers of a nucleic acid or salt selected from the group consisting of deoxyribonucleic acid, a pharmaceutically acceptable salt of deoxyribonucleic acid, ribonucleic acid, a pharmaceutically acceptable salt of ribonucleic acid, and a combination thereof.

2. A method in accordance with claim 1, wherein said nucleic acid or salt is administered in an amount of 0.001 to 100 mg per dose, with a 1- to 7-day interval between doses.

3. A method in accordance with claim 1, wherein said nucleic acid or salt comprises deoxyribonucleic acid or a pharmaceutically acceptable salt thereof, substantially free of ribonucleic acid or salt.

4. A method in accordance with claim 1, wherein said nucleic acid or salt is obtained from *Mycobacterium bovis* strain BCG.

5. A method in accordance with claim 4, wherein said strain is *Mycobacterium bovis* BCG, ATCC 19015.

6. A method in accordance with claim 1, wherein said nucleic acid or salt is obtained from *Bacillus subtilis*, ATCC 6633.

7. A method in accordance with claim 1, wherein the route of administration of said nucleic acid or salt is intradermal, hypodermic, intramuscular, intravenous, oral or direct administration to the situs of the digestive ulcer.

8. A method in accordance with claim 1, wherein said nucleic acid or salt comprises a combination of deoxyribonucleic acid or a pharmaceutically acceptable salt thereof and ribonucleic acid or pharmaceutically acceptable salt thereof, said combination containing more of said deoxyribonucleic acid or salt than said ribonucleic acid or salt.

9. A method in accordance with claim 1, wherein said nucleic acid or salt is obtained from a bacterial BC97G strain.

* * * * *